United States Patent
Roh et al.

(10) Patent No.: US 11,434,215 B2
(45) Date of Patent: Sep. 6, 2022

(54) EPOXY REACTIVE DILUENT AND MANUFACTURING METHOD THEREFOR

(71) Applicant: KOREA KUMHO PETROCHEMICAL CO., LTD., Seoul (KR)

(72) Inventors: Kee Yoon Roh, Daejeon (KR); Nam Hyun Cho, Daejeon (KR); Jung Hee Jang, Daejeon (KR); Yuncheol Park, Asan-Si (KR)

(73) Assignee: KOREA KUMHO PETROCHEMICAL CO., LTD., Seoul (KR)

( * ) Notice: Subject to any disclaimer, the term of this patent is extended or adjusted under 35 U.S.C. 154(b) by 0 days.

(21) Appl. No.: 17/048,444

(22) PCT Filed: May 22, 2019

(86) PCT No.: PCT/KR2019/006116
§ 371 (c)(1),
(2) Date: Oct. 16, 2020

(87) PCT Pub. No.: WO2019/240396
PCT Pub. Date: Dec. 19, 2019

(65) Prior Publication Data
US 2021/0163435 A1    Jun. 3, 2021

(30) Foreign Application Priority Data
Jun. 12, 2018 (KR) .......... 10-2018-0067408

(51) Int. Cl.
C07D 303/28 (2006.01)
C07D 301/28 (2006.01)
C07D 301/32 (2006.01)
C09D 7/20 (2018.01)

(52) U.S. Cl.
CPC ......... *C07D 303/28* (2013.01); *C07D 301/28* (2013.01); *C07D 301/32* (2013.01); *C09D 7/20* (2018.01)

(58) Field of Classification Search
CPC .................................. C07D 303/28
See application file for complete search history.

(56) References Cited

FOREIGN PATENT DOCUMENTS

| CN | 1374299 A | * 10/2002 |
| CN | 1374299 A | 10/2002 |
| CN | 102558102 A | 7/2012 |
| KR | 10-2011-0115635 A | 10/2011 |
| KR | 10-2015-0088612 A | 8/2015 |
| KR | 20150088612 A | 8/2015 |
| WO | 2016-183794 A1 | 11/2016 |

OTHER PUBLICATIONS

Braga et al. Dyes and Pigments 2017, 141, 235-244 (Year: 2017).*
Cardolite, Cardolite® Lite 2513HP Technical Datasheet, Mar. 2009 (Year: 2009).*
Cardolite, Cardolite® NC-513 Technical Datasheet, Mar. 2009 (Year: 2009).*
Suresh et al. Ind. Eng. Chem. Res. 2005, 44, 4504-4512 (Year: 2005).*
Patel, M. B. et al. "Glass-fibre-reinforced epoxy composites using epoxidized cardanol as diluent", High Performance Polymers, 1991, pp. 107-111, vol. 3, No. 2.
Patel et al., "Curing Kinetics of Epoxy Resin Using Epoxidized Cardanol as Diluent With/Without Fortifier", Elsevier Science Publishers, 1988, pp. 277-284.

* cited by examiner

*Primary Examiner* — Matthew P Coughlin
(74) *Attorney, Agent, or Firm* — Novick, Kim & Lee, PLLC; Jae Youn Kim

(57) ABSTRACT

Provided is an epoxy reactive diluent, wherein the content of a compound represented by Formula 1 below is 85% by weight or more based on a total weight of an epoxy reactive diluent composition:

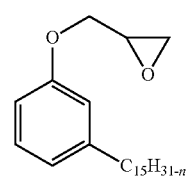

[Formula 1]

wherein n is 0, 2, 4 or 6.

1 Claim, 4 Drawing Sheets

EPOXY REACTIVE DILUENT AND MANUFACTURING METHOD THEREFOR

TECHNICAL FIELD

The present invention relates to an epoxy reactive diluent and a method of preparing the same, and more particularly to an epoxy reactive diluent including epoxidized cardanol and a method of preparing the same.

BACKGROUND ART

Conventionally, various components including epoxy components such as benzyl glycidyl ether, n-butyl glycidyl ether, phenyl glycidyl ether, o-cresyl glycidyl ether, aliphatic glycidyl ether, etc. have been added as plasticizers and diluents for epoxy paint. Such components, which are added as reactive diluents to epoxy paint, have been used to impart plasticity or adjust pot-life.

Thereamong, epoxidized cardanol, i.e., cardanol glycidyl ether, produced using cardanol as a raw material extracted from natural cashew nuts has an epoxy functional group in a molecular structure thereof, thereby being capable of providing excellent film properties during the hardening reaction of epoxy paint. In addition, unsaturated hydrocarbon chains of cardanol can facilitate crosslinking, thereby being capable of improving the strength, flexibility and heat resistance of a film. The structure of epoxidized cardanol is shown in Formula 1 below:

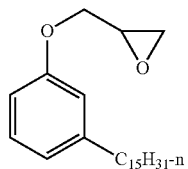

[Formula 1]

wherein Formula 1, n is 0, 2, 4 or 6.

FIG. 1 illustrates a method of extracting a cardanol raw material from cashew nuts. Cardanol extracted by such a method has a hydrocarbon chain at a meta position of a phenolic hydroxy group thereof. Epoxidized cardanol can be obtained by reacting cardanol with epicholorhydrin in the presence of an alkylation catalyst. This reaction has been conventionally performed in the presence of an aqueous solution or a dimethyl sulfoxide solvent. In addition, a base such as sodium hydroxide, potassium hydroxide, sodium carbonate, potassium carbonate, sodium hydride, etc. has been used as a catalyst, and a phase transfer catalyst such as tetra-n-butylammonium chloride, etc. as a subcatalyst for reaction activation has been added. After completion of the reaction, epoxidized cardanol was extracted using an organic solvent, and reaction byproducts were removed through a washing process so as to improve the purity of a diluent.

Nevertheless, existing technologies have problems that the purity of a desired product, epoxidized cardanol, is low due to the high content of reaction byproducts, and it is difficult to treat wastewater generated in an extraction process using an organic solvent. In addition, in the case of some technologies, products may be hydrolyzed due to a long reaction time, and thus reaction byproducts increase, resulting in increases in viscosity and epoxy equivalent weight.

DISCLOSURE

Technical Problem

Therefore, the present invention has been made in view of the above problems, and it is one object of the present invention to provide an epoxy reactive diluent having high purity and low viscosity and a low epoxy equivalent weight through minimization of hydrolysis and side reactions and a method of preparing the same.

It is another object of the present invention to provide a method of preparing an epoxy reactive diluent that is extracted without use of an organic solvent and thus does not require a washing process causing waste water.

Technical Solution

In accordance with an aspect of the present invention, the above and other objects can be accomplished by the provision of an epoxy reactive diluent, wherein a content of a compound represented by Formula 1 below is 85% by weight or more based on a total weight of an epoxy reactive diluent composition:

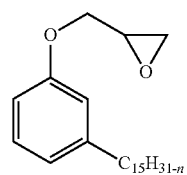

[Formula 1]

wherein n is 0, 2, 4 or 6.

In an embodiment, contents of cardanol, a compound represented by Formula 2 below, a compound represented by Formula 3 below, and a compound represented by Formula 4 below in the composition may be respectively less than 2% by weight, less than 5% by weight, less than 5% by weight, and less than 4% by weight:

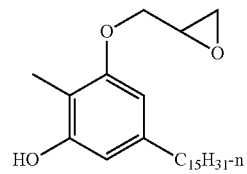

[Formula 2]

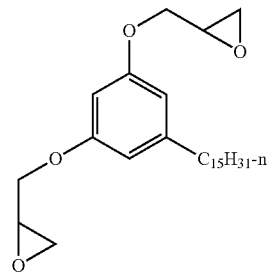

[Formula 3]

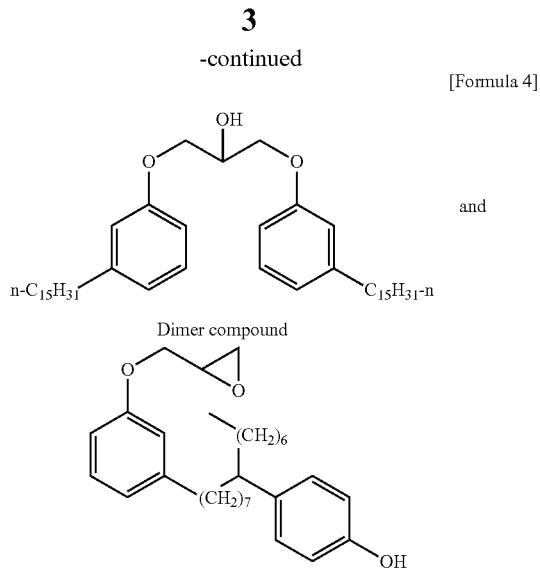

wherein, Formulas 2 to 4, n is 0, 2, 4 or 6.

In an embodiment, the composition may have a viscosity of 40 to 90 cps at 25° C.

In accordance with another aspect of the present invention, there is provided a method of preparing an epoxy reactive diluent, the method including: (a) a step of reacting a mixture including cardanol and epicholorhydrin in a presence of a catalyst to obtain a product in which a content of epoxidized cardanol is 85% by weight or more; and (b) a step of isolating and purifying the product.

In an embodiment, the catalyst may be a base.

In an embodiment, the base may be one selected from the group consisting of NaOH, KOH, $Na_2CO_3$, $K_2CO_3$, NaH and a combination of two or more thereof.

In an embodiment, the base may be a 1 to 60% by weight aqueous solution.

In an embodiment, in step (a), the catalyst may be added dropwise to the mixture for 45 to 135 minutes, followed by allowing a reaction to occur for 60 to 180 minutes.

In an embodiment, an equivalent ratio of the cardanol to the epicholorhydrin may be 1:1 to 1:10.

In an embodiment, in step (a), an equivalent ratio of the cardanol to the catalyst may be 1:0.1 to 1:1.5.

In an embodiment, step (b) may include (b1) a step of filtering the product to obtain a filtrate; (b2) a step of separating the filtrate into an upper layer and a lower layer to remove the lower layer; (b3) a step of vacuum-evaporating the upper layer to recover epicholorhydrin; and (b4) a step of filtering a product generated in the vacuum-evaporating.

In an embodiment, in step (b2), layer separation may be performed by allowing the filtrate to stand for 60 to 180 minutes without addition of an organic solvent.

In an embodiment, in step (b3), the vacuum-evaporating may be performed at 100 to 120° C.

Advantageous Effects

In accordance with an aspect of the present invention, an epoxy reactive diluent having high purity and low viscosity and a low epoxy equivalent weight through minimization of hydrolysis and side reactions and a method of preparing the same can be provided.

In accordance with another aspect of the present invention, a method of preparing an epoxy reactive diluent that is extracted without use of an organic solvent and thus does not require a washing process causing waste water can be provided.

It should be understood that the effects of the present invention are not limited to the effects described above, but include all effects that can be deduced from the detailed description of the present invention or the constitution of the invention described in the claims.

Modes of the Invention

Figure 1:
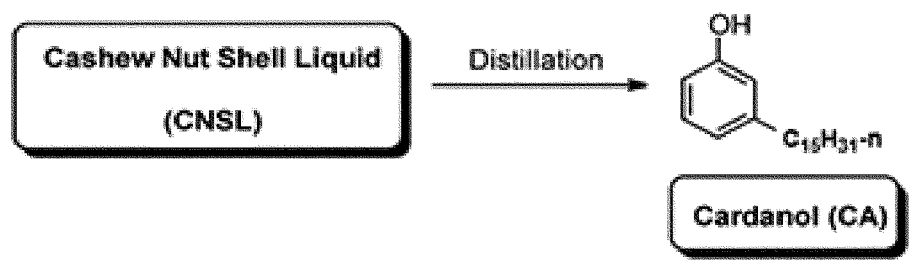
FIG. 1 is a schematic diagram illustrating a method of obtaining cardanol from natural cashew nuts.

Exemplary embodiments of the present invention are described in detail with reference to the accompanying drawings. However, the present invention may be implemented in various different forms and is not limited to these embodiments. To clearly describe the present invention, a part unrelated to the description is omitted in the drawings, and like reference numerals in the specification denote like elements.

In the specification, when it is described that a certain part is "connected" to another part, it should be understood that the certain part may be directly connected to the other part or indirectly connected to the other part via another part therebetween. In addition, when a certain part "includes" a certain component, this indicates that the part may further include another component instead of excluding the other component unless otherwise disclosed.

In the present specification, "reactive diluent" refers to an additive used to reduce the viscosity of epoxy paint. A reactive diluent participates in a hardening reaction during hardening of the epoxy paint to form a portion of a cross-linked structure.

"Plasticity" refers to a deformation property of a material by an external force. In the case of materials having low plasticity, cracks can be easily generated even by a weak external force. When the diluent is added to impart plasticity, the flexibility and heat resistance of the epoxy paint can be increased.

"Pot-life" refers to the time during which two or more components maintain appropriate fluidity and adhesion without being gelated or hardened. The pot-life of the epoxy paint may be controlled by adjusting the content of the diluent.

"Epoxy equivalent weight" refers to the weight of a resin including 1 equivalent of an epoxy group. The number of epoxy groups in a resin decreases with an increasing epoxy equivalent weight value.

Hereinafter, an embodiment of the present invention is described in detail with reference to the accompanying drawings.

With regard to an epoxy reactive diluent according to an aspect of the present invention, the content of a compound represented by Formula 1 below may be 85% by weight or more based on a total weight of an epoxy reactive diluent composition:

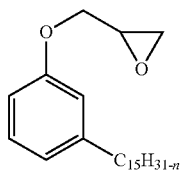

Figure 2:
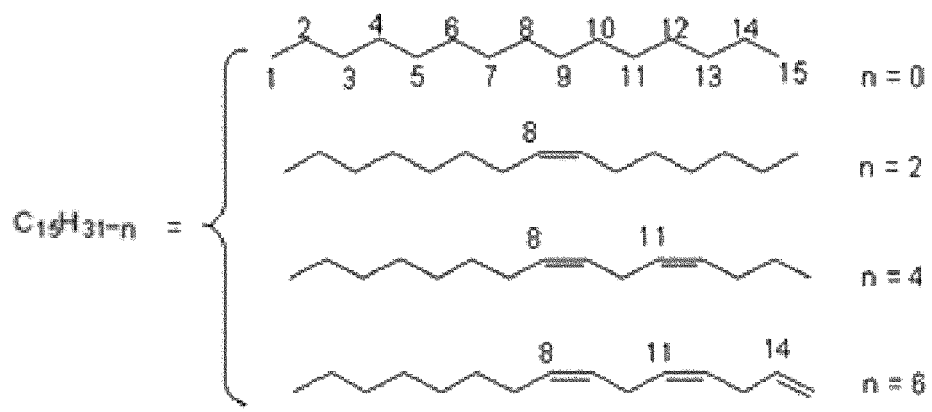
FIG. 2 illustrates hydrocarbon chains of epoxidized cardanol prepared according to an embodiment of the present invention.

[Formula 1]

wherein n may be 0, 2, 4 or 6. $C_{15}H_{31}$-n chain structures according to the n value are illustrated in FIG. 2.

The diluent may be added to an epoxy paint to impart plasticity thereto and control the pot-life thereof during a hardening reaction.

Figure 3:
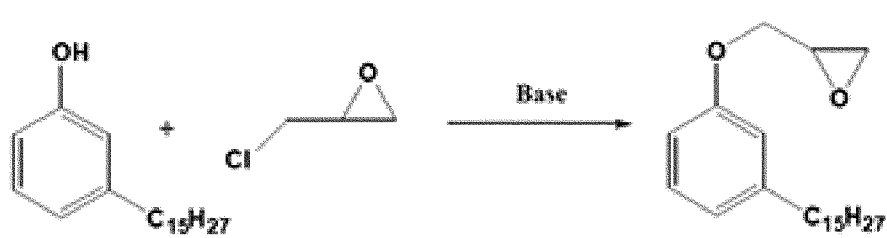
FIG. 3 illustrates an epoxidized cardanol generation reaction according to an embodiment of the present invention.

FIG. 1 is a schematic diagram illustrating a method of obtaining cardanol from natural cashew nut shells, and FIG. 3 illustrates a reaction scheme wherein the compound represented by Formula 1 is generated by reacting the cardanol.

In a process of obtaining the cardanol, cardol and 2-methyl cardol by-products represented by Formulas 5 and 6 below may be obtained. An appearance color of the cardanol may be changed depending upon the contents of the cardol and the 2-methyl cardol.

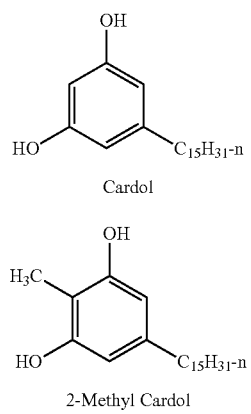

[Formula 5]

Cardol

[Formula 6]

2-Methyl Cardol

Referring to FIG. 3, the compound represented by Formula 1 may be prepared by reacting the cardanol and epicholorhydrin in the presence of a base. Based on a total weight of the composition, the content of the compound represented by Formula 1 may be 85% by weight or more, and the content of unreacted cardanol may be less than 2% by weight.

Figure 4:
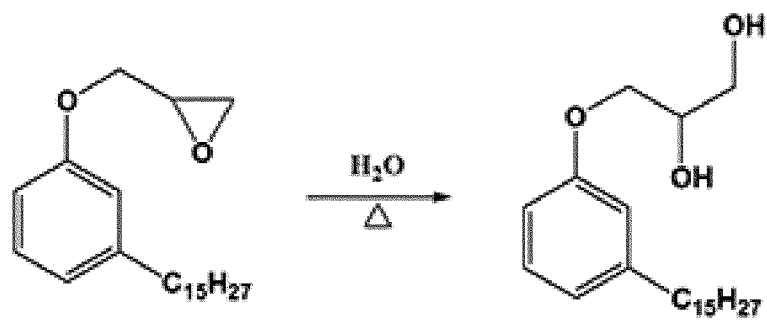
FIG. 4 illustrates a reaction wherein epoxidized cardanol prepared according to an embodiment of the present invention is hydrolyzed so that reaction byproducts are generated.
Figure 5:
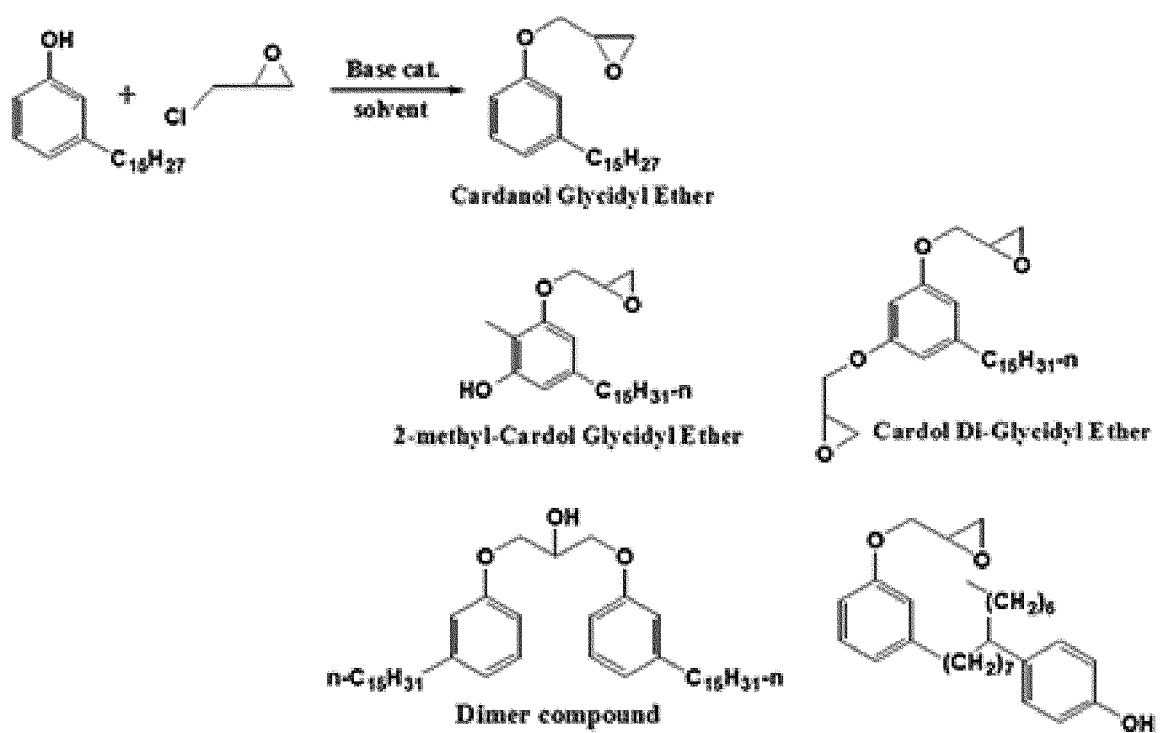
FIG. 5 illustrates a reaction scheme wherein epoxidized cardanol and reaction byproducts are generated according to an embodiment of the present invention.

FIG. 4 illustrates a reaction scheme wherein the compound represented by Formula 1 is hydrolyzed so that reaction byproducts are generated, and FIG. 5 illustrates a reaction scheme wherein the compound represented by Formula 1 and compounds represented by Formulas 2 to 4 below are generated by reacting the cardanol.

Referring to FIG. 4, the compound represented by Formula 1 may be easily hydrolyzed under a water condition to form 3-cardanoxy-1,2-propanediol as a reaction byproduct, which may increase an epoxy equivalent weight value of the composition. When an epoxy equivalent weight value increases, hardening reaction characteristics of epoxy paint may be decreased. Accordingly, the properties of epoxy paint may be increased by reducing the content of the reaction byproducts.

Based on a total weight of the composition, the contents of cardanol, a compound represented by Formula 2 below, a compound represented by Formula 3 below, and a compound represented by Formula 4 below may be respectively less than 2% by weight, less than 5% by weight, less than 5% by weight, and less than 4% by weight:

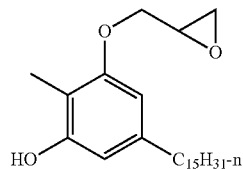

[Formula 2]

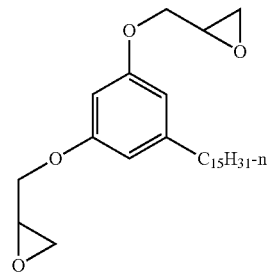

[Formula 3]

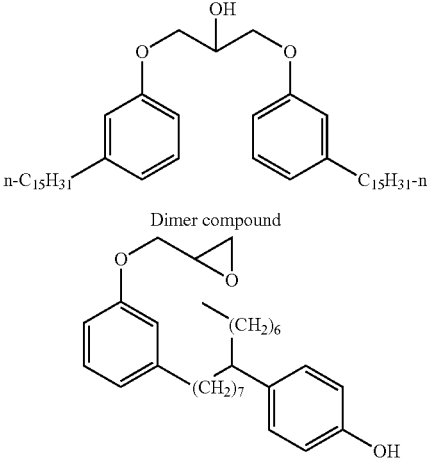

[Formula 4]

and

Dimer compound

In Formulas 2 to 4, n may be 0, 2, 4 or 6. A $C_{15}H_{31-n}$ chain structure according to the n value may be the same as the compound represented by Formula 1.

The cardanol may be a product which does not react during the preparation of the composition.

The compound represented by Formula 2 is 2-methylcardol glycidyl ether. The compound represented by Formula 3 is cardol-diglycidyl ether. The compound represented by Formula 4 is a dimer and may include both the compounds with different structures shown in Formula 4.

Referring to FIG. 5, the viscosity of the composition increases as the contents of the compound represented by Formula 2, the compound represented by Formula 3, and the compound represented by Formula 4 increase, so that viscosity control characteristics may be decreased. Accordingly, the properties of epoxy paint may be improved by lowering the contents of the compound represented by Formula 2, the compound represented by Formula 3 and the compound represented by Formula 4. The viscosity of the composition may be 40 to 90 cps, preferably 40 to 60 cps, at 25° C.

The composition may not include organic solvents such as methanol, ethanol, isopropanol, acetone, toluene and dimethyl sulfoxide. When the organic solvents are included, organic solvent waste water may be generated in a process of preparing a diluent, resulting in environmental pollution.

A method of preparing an epoxy reactive diluent according to another embodiment of the present invention may include (a) a step of reacting a mixture including cardanol and epicholorhydrin in the presence of a catalyst to obtain a product in which the content of epoxidized cardanol is 85% by weight or more; and (b) a step of isolating and purifying the product.

The epicholorhydrin may be used as a reactant and a solvent at the same time. A product generated by performing the reaction, illustrated in FIG. 3, is hydrolyzed in an aqueous solution and reaction byproducts are generated, by a reaction illustrated in FIG. 4, so that an epoxy equivalent weight value of a produced diluent may increase. Addition of an organic solvent such as dimethyl sulfoxide or methanol may cause environmental destruction and an increase in generation amounts of the compound represented by Formula 2, the compound represented by Formula 3 and the compound represented by Formula 4.

The catalyst may be a base. The base may be one selected from the group consisting of NaOH, KOH, $Na_2CO_3$, $K_2CO_3$, NaH and a combination of two or more thereof, preferably, NaOH.

The base may be a 1 to 60% by weight aqueous solution, preferably, a 30 to 50% by weight aqueous solution. When the concentration of the base is less than 1% by weight, a reaction time increases so that a generation amount of reaction byproducts may increase due to hydrolysis. When the concentration of the base is greater than 60% by weight, there may be a problem in controlling a reaction temperature in step (a).

In step (a), the catalyst may be added dropwise to the mixture for 45 to 135 minutes, followed by allowing a reaction to occur for 60 to 180 minutes. When the catalyst is added dropwise for less than 45 minutes, the temperature of the mixture rapidly increases and thus safety accidents may occur. When the catalyst is added dropwise for greater than 135 minutes, a generation amount of reaction byproducts may increase due to hydrolysis. When the reaction is performed for less than 60 minutes, a reaction yield may be decreased. When the reaction is performed for greater than 180 minutes, the epoxy equivalent weight and viscosity of a produced diluent may excessively increase.

An equivalent ratio of the cardanol to the epicholorhydrin may be 1:1 to 1:10, preferably, 1:2 to 1:5. When the equivalent of the epicholorhydrin is less than 1, the content of unreacted cardanol in an obtained product may increase. When the equivalent of the epicholorhydrin is greater than 10, resources for recovering the epicholorhydrin may be excessively consumed.

An equivalent ratio of the cardanol to the catalyst may be 1:0.1 to 1:1.5. When the equivalent of the catalyst is less than 0.1, a reaction may not smoothly proceed. When the equivalent of the catalyst is greater than 1.5, a generation amount of reaction byproducts may increase.

Step (b) may include (b1) a step of filtering the product to obtain a filtrate; (b2) a step of separating the filtrate into an upper layer and a lower layer to remove the lower layer; (b3) a step of vacuum-evaporating the upper layer to recover epicholorhydrin; and (b4) a step of filtering a product generated in step (b3).

In step (Ill), the catalyst and metal chloride salts generated from epicholorhydrin may be removed. For example, when NaOH is used as a catalyst, NaCl may be removed through filtration. The filtration may be performed using a metal filter net with a pore size of 1 to 100 μm, preferably, 10 to 30 μm.

In step (b2), the filtrate is injected into a separatory funnel, followed by being allowed to stand for 60 to 180 minutes without addition of an organic solvent. As a result, the filtrate is separated into an upper layer and a lower layer. Since the product is present in the upper layer, the lower layer, as a water-soluble layer, may be removed. The present invention extracts a product without addition of an organic solvent and a separate washing process, thereby being ecofriendly.

The vacuum evaporation of step (b3) may be performed at 100 to 120° C. to recover a volatile material. The evaporated and recovered epicholorhydrin may be recycled.

In step (b4), filtration may be performed in the same manner as in step (b1) to remove a trace amount of remaining metal chloride salts.

Hereinafter, embodiments of the present invention will be described in more detail. However, the following experimental results correspond to representative experimental results of the embodiments, and the scope and content of the present invention should not be interpreted as being reduced or limited by the embodiments and the like. The effects of each of various embodiments of the invention, which are not explicitly set forth below, will be described in detail in a corresponding section.

The following experimental results show comparison results of the properties and compositions of an epoxy reactive diluent prepared according to an embodiment of the present invention and an epoxy reactive diluent prepared according to a conventional method.

EXAMPLE

Cardanol (720 g, 1.0 eq) and epicholorhydrin (670 g, 3.0 eq) were fed into a reactor, and 40% NaOH (337.7 g, 1.0 eq) was added thereto dropwise for 90 minutes until a reaction temperature increased from 20° C. to 70° C. After completing the addition of NaOH, the reactants were further reacted for 2 hours while maintaining a reaction temperature of the reactants at 55 to 60° C., thereby obtaining a solution including epoxidized cardanol. The solution was analyzed by gas chromatography (GC). As a result, the solution was analyzed to be constituted of 1.2% unreacted cardanol, 85.9% epoxidized cardanol, 4.2% 2-methyl-cardol glycidyl ether, 4.7% cardol-diglycidyl ether, and 3.6% dimer.

Next, the obtained solution was filtered to remove a sodium chloride salt. The resultant filtrate was injected into a separatory funnel, followed by allowing layer separation to occur for 1 hour. A separated lower layer was removed, and a separated upper layer was fed into a reactor, followed by vacuum-evaporating at 120° C. to remove water and unreacted epicholorhydrin. The resultant concentrate was filtered to remove a sodium chloride salt, thereby obtaining an epoxy reactive diluent.

Comparative Example 1

Cardanol (720 g, 1.0 eq) and epicholorhydrin (670 g, 3.0 eq) were fed into a reactor, and 40% NaOH (405 g, 1.2 eq)

was added thereto dropwise for 90 minutes until a reaction temperature increased from 50° C. to 90° C. After completing the addition of NaOH, the reactants were further reacted for 2 hours while maintaining a reaction temperature of the reactants at 60 to 65° C., thereby obtaining a solution including epoxidized cardanol. The solution was analyzed by gas chromatography (GC). As a result, the solution was analyzed to be constituted of 1.4% unreacted cardanol, 81.8% epoxidized cardanol, 7.1% 2-methyl-cardol glycidyl ether, 6.8% cardol-diglycidyl ether, and 2.6% dimer.

Next, the obtained solution was filtered to remove a sodium chloride salt. The resultant filtrate was injected into a separatory funnel, followed by allowing layer separation to occur for 1 hour. A separated lower layer was removed, and a separated upper layer was fed into a reactor, followed by vacuum-evaporating at 120° C. to remove water and unreacted epicholorhydrin. The resultant concentrate was filtered to remove a sodium chloride salt, thereby obtaining an epoxy reactive diluent.

Comparative Example 2

Cardanol (720 g, 1.0 eq) and epicholorhydrin (670 g, 3.0 eq) were fed into a reactor, and 50% NaOH (347.4 g, 1.2 eq) was added thereto dropwise for 90 minutes until a reaction temperature increased from 50° C. to 90° C. After completing the addition of NaOH, the reactants were further reacted for 2 hours while maintaining a reaction temperature of the reactants at 60 to 65° C., thereby obtaining a solution including epoxidized cardanol. The solution was analyzed by gas chromatography (GC). As a result, the solution was analyzed to be constituted of 3.6% unreacted cardanol, 81.7% epoxidized cardanol, 6.9% 2-methyl-cardol glycidyl ether, 5.6% cardol-diglycidyl ether, and 2.2% dimer.

Next, the obtained solution was filtered to remove a sodium chloride salt. The resultant filtrate was injected into a separatory funnel, followed by allowing layer separation to occur for 1 hour. A separated lower layer was removed, and a separated upper layer was fed into a reactor, followed by vacuum-evaporating at 120° C. to remove water and unreacted epicholorhydrin. The resultant concentrate was filtered to remove a sodium chloride salt, thereby obtaining an epoxy reactive diluent.

Comparative Example 3

Cardanol (720 g, 1.0 eq) and epicholorhydrin (670 g, 3.0 eq) were fed into a reactor, and 30% NaOH (501.8 g, 1.2 eq) was added thereto dropwise for 90 minutes until a reaction temperature increased from 50° C. to 90° C. After completing the addition of NaOH, the reactants were further reacted for 2 hours while maintaining a reaction temperature of the reactants at 60 to 65° C., thereby obtaining a solution including epoxidized cardanol. The solution was analyzed by gas chromatography (GC). As a result, the solution was analyzed to be constituted of 3.9% unreacted cardanol, 80.7% epoxidized cardanol, 7.7% 2-methyl-cardol glycidyl ether, 5.9% cardol-diglycidyl ether, and 1.68% dimer.

Next, the obtained solution was filtered to remove a sodium chloride salt. The resultant filtrate was injected into a separatory funnel, followed by allowing layer separation to occur for 1 hour. A separated lower layer was removed, and a separated upper layer was fed into a reactor, followed by vacuum-evaporating at 120° C. to remove water and unreacted epicholorhydrin. The resultant concentrate was filtered to remove a sodium chloride salt, thereby obtaining an epoxy reactive diluent.

Comparative Example 4

Cardanol (720 g, 1.0 eq), acetone (576 g, 0.8 part by weight based on 1 part by weight of cardanol), and NaOH (96.5 g, 1.0 eq) were fed into a reactor, and epicholorhydrin (401.7 g, 1.8 eq) was added thereto for 90 minutes until a reaction temperature increased from 50° C. to 70° C. After completing the addition of epicholorhydrin, the reactants were further reacted for 2 hours while maintaining a reaction temperature of the reactants at 60 to 65° C., thereby obtaining a solution including epoxidized cardanol. The solution was analyzed by gas chromatography (GC). As a result, the solution was analyzed to be constituted of 3.3% unreacted cardanol, 78.6% epoxidized cardanol, 2.9% 2-methyl-cardol glycidyl ether, 4.1% cardol-diglycidyl ether, and 11.1% dimer.

Next, the solution was vacuum-evaporated at 120° C. to remove acetone and unreacted epicholorhydrin. The resultant concentrate was filtered to remove a sodium chloride salt, thereby obtaining an epoxy reactive diluent.

Comparative Example 5

Cardanol (720 g, 1.0 eq) and epicholorhydrin (670 g, 3.0 eq) were fed into a reactor, and 50% potassium hydroxide (487.2 g, 1.2 eq) was added thereto dropwise for 90 minutes until a reaction temperature increased from 50° C. to 90° C. After completing the addition of potassium hydroxide, the reactants were further reacted for 2 hours while maintaining a reaction temperature of the reactants at 60 to 65° C., thereby obtaining a solution including epoxidized cardanol. The solution was analyzed by gas chromatography (GC). As a result, the solution was analyzed to be constituted of 4.8% unreacted cardanol, 76.5% epoxidized cardanol, 9.8% 2-methyl-cardol glycidyl ether, 6.0% cardol-diglycidyl ether, and 3.6% dimer.

Next, the obtained solution was filtered to remove a sodium chloride salt. The resultant filtrate was injected into a separatory funnel, followed by allowing layer separation to occur for 1 hour. A separated lower layer was removed, and a separated upper layer was fed into a reactor, followed by vacuum-evaporating at 120° C. to remove water and unreacted epicholorhydrin. The resultant concentrate was filtered to remove a sodium chloride salt, thereby obtaining an epoxy reactive diluent.

Next, the obtained solution was filtered to remove a potassium chloride salt. The resultant filtrate was injected into a separatory funnel, followed by allowing layer separation to occur for 1 hour. A separated lower layer was removed, and a separated upper layer was fed into a reactor, followed by vacuum-evaporating at 120° C. to remove water and unreacted epicholorhydrin. The resultant concentrate was filtered to remove a potassium chloride salt, thereby obtaining an epoxy reactive diluent.

The epoxy reactive diluent prepared according to the example and a conventional epoxy reactive diluent product (NC-513, Cardolite) were subjected to GC measurement and compared to each other. Results are shown in FIG. 6.

Figure 6:
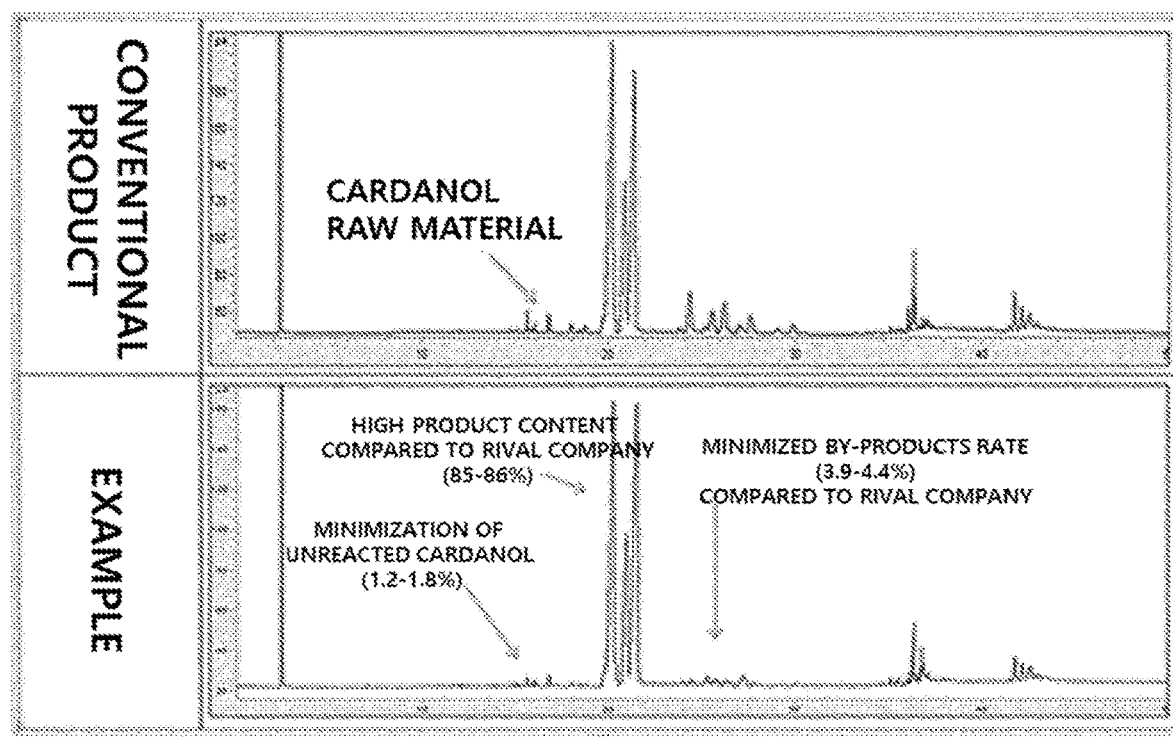
FIG. 6 illustrates gas chromatography results of a conventional epoxy reactive diluent (a conventional product) and an epoxy reactive diluent prepared according to an embodiment of the present invention.

Referring to FIG. 6, it was confirmed that the diluent prepared according to the example exhibited high purity due to a high product content and low contents of unreacted cardanol and by-products, compared to the conventional product.

The aforementioned description of the present invention is provided by way of example and those skilled in the art will understand that the present invention can be easily changed or modified into other specified forms without change or modification of the technical spirit or essential characteristics of the present invention. Therefore, it should be understood that the aforementioned examples are only provided by way of example and not provided to limit the present invention. For example, each of constituents described as a single form may be separately implemented and, similarly, constituents described as being separated may be implemented in a combined form.

It should be understood that the scope of the present invention is defined by the following claims and the invention is to cover all modifications, equivalents, and alternatives falling within the spirit and scope of the invention as defined by the claims.

The invention claimed is:

1. An epoxy reactive diluent, wherein a content of a compound represented by Formula 1 below is 85% by weight or more based on a total weight of the epoxy reactive diluent:

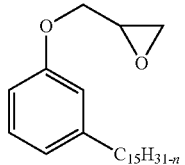

[Formula 1]

wherein n is 2 or 6;

the contents of cardanol, a compound represented by Formula 2 below, a compound represented by Formula 3 below, and a compound represented by Formula 4 below in the epoxy reactive diluent are respectively less than 2% by weight, less than 5% by weight, less than 5% by weight, and less than 4% by weight:

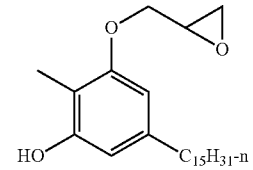

[Formula 2]

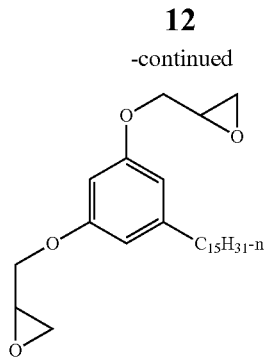

[Formula 3]

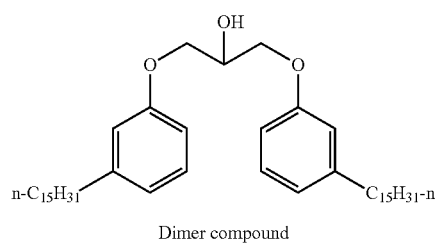

[Formula 4]

and

Dimer compound

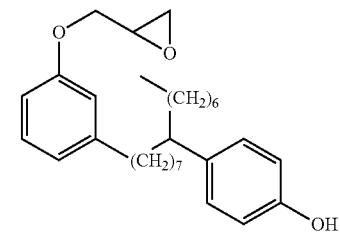

wherein, in Formulas 2 to 4, n is 0, 2, 4 or 6; and
the epoxy reactive diluent has a viscosity of 40 to 90 cps at 25° C.

* * * * *